US011100413B2

(12) United States Patent
Spangler et al.

(10) Patent No.: US 11,100,413 B2
(45) Date of Patent: *Aug. 24, 2021

(54) COMBINING CHEMICAL STRUCTURE DATA WITH UNSTRUCTURED DATA FOR PREDICTIVE ANALYTICS IN A COGNITIVE SYSTEM

(71) Applicant: International Business Machines Corporation, Armonk, NY (US)

(72) Inventors: William S. Spangler, San Martin, CA (US); Richard L. Martin, Jamaica Plain, MA (US); Feng Wang, Santa Clara, CA (US); Xiaoyang Gao, San Jose, CA (US); Sheng Hua Bao, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 177 days.

This patent is subject to a terminal disclaimer.

(21) Appl. No.: 16/444,131

(22) Filed: Jun. 18, 2019

(65) Prior Publication Data

US 2019/0303780 A1    Oct. 3, 2019

Related U.S. Application Data

(63) Continuation of application No. 15/895,256, filed on Feb. 13, 2018.

(51) Int. Cl.
*G06F 3/048* (2013.01)
*G06N 5/04* (2006.01)
(Continued)

(52) U.S. Cl.
CPC ........... *G06N 5/043* (2013.01); *G06F 16/338* (2019.01); *G06F 16/3347* (2019.01); *G06N 20/00* (2019.01); *G16C 20/70* (2019.02)

(58) Field of Classification Search
CPC .... G06N 5/043; G06N 20/00; G06F 16/3347; G06F 16/338; G16C 20/70
See application file for complete search history.

(56) References Cited

U.S. PATENT DOCUMENTS 6,904,423 B1 *  6/2005  Nicolaou ................. G06N 5/02
                                                                706/46
10,013,467 B1 *  7/2018  Brogle .................... G16C 20/80
(Continued)

OTHER PUBLICATIONS

List of IBM Patents or Patent Applications Treated as Related, filed Jun. 18, 2019.

*Primary Examiner* — David Phantana-angkool
(74) *Attorney, Agent, or Firm* — Will Stock; Edell, Shapiro & Finnan, LLC (57) ABSTRACT

According to embodiments of the present invention, an entity may be represented by an unstructured feature vector comprising a plurality of features extracted from unstructured data using semantic analysis and a structural feature vector comprising a plurality of features from chemical structure data. A similarity matrix may be used to compare entities and generate a similarity score, based on both the unstructured feature vector and the structural feature vector for each entity. In some aspects, a user may enter a query (from which a chemical structural feature vector is dynamically generated) to compare against entities having unstructured and/or structural feature vectors, stored in a database.

7 Claims, 6 Drawing Sheets

(51) Int. Cl.
    *G06N 20/00*     (2019.01)
    *G06F 16/338*     (2019.01)
    *G06F 16/33*     (2019.01)
    *G16C 20/70*     (2019.01)

(56) References Cited

U.S. PATENT DOCUMENTS

| | | |
|---|---|---|
| 10,503,786 B2 | 12/2019 | Allen et al. |
| 10,762,538 B2 | 9/2020 | Shi-Nash et al. |
| 10,803,121 B2 | 10/2020 | Jin et al. |
| 10,810,234 B2 | 10/2020 | Han et al. |
| 10,817,614 B2 | 10/2020 | Burch et al. |
| 10,891,277 B2 | 1/2021 | Botea et al. |
| 10,902,351 B1 | 1/2021 | Neumann |
| 2007/0043511 A1* | 2/2007 | Jensen .................. G16C 20/80 702/19 |
| 2010/0155078 A1* | 6/2010 | Walters .................. G16C 20/30 166/369 |
| 2014/0280224 A1* | 9/2014 | Feinberg ............ G06F 16/9024 707/748 |
| 2015/0324454 A1* | 11/2015 | Roberts ............... G06F 16/9032 707/734 |
| 2017/0076041 A1 | 3/2017 | Zhou et al. |
| 2019/0251455 A1* | 8/2019 | Spangler ................ G06F 16/338 |
| 2021/0057100 A1 | 2/2021 | Neumann |
| 2021/0081458 A1 | 3/2021 | Neumann |

\* cited by examiner

COMBINING CHEMICAL STRUCTURE DATA WITH UNSTRUCTURED DATA FOR PREDICTIVE ANALYTICS IN A COGNITIVE SYSTEM

BACKGROUND

1. Technical Field

Present invention embodiments relate to predictive analytics, and more specifically, to utilizing both structural data and unstructured data to generate complex predictions in a cognitive system.

2. Discussion of the Related Art

In the modern computing era, computational techniques and systems allow for complex analysis on large volumes or corpuses of data. Cognitive and machine learning systems in combination with natural language processing techniques may be used to extract, analyze, and make inferences or predictions from large sets of data.

Current approaches typically limit data analysis to a single type of data, using either unstructured data or structural data in isolation to make predictions. For unstructured data analysis, data concepts or properties may be represented by features mined from the occurrences of those data concepts in unstructured data, such as text. However, this approach limits the representation of data concepts to those that are able to be presented with unstructured data, and does not capture other relevant properties such as those based on chemical structure. For example, unstructured text-based analytics cannot adequately capture, represent and differentiate certain physical and structural properties of entities, and cannot be used for entities which have a structural representation but do not occur in any available unstructured text.

For structural data analysis, data concepts or properties are based on chemical structure information of an entity. However, this type of approach limits features to those that are able to be described by structural data, and does not consider other relevant features, e.g., emergent chemical or biological properties, applications of chemical compounds, etc., that may be represented using unstructured data. Chemical structure-based analytics alone cannot adequately capture, represent and differentiate certain properties of chemical entities, and cannot represent entities with only an unstructured representation, such as compounds with no available structure information, compounds that are not easily represented by a chemical structure such as macromolecules, or entities that are not chemical compounds.

Thus, existing methods for similarity-based analytics typically utilize only one type of entity representation, structural or unstructured, and as such are limited to either chemical structure-based analytics or text-based analytics. Accordingly, such techniques, which constrain predictive analytics to a single dimension of data, are limited in their ability to make complex predictions. Existing predictive analytics applications typically do not utilize both structured and unstructured data for analytics purposes, as these types of information are distinct and challenging to combine.

SUMMARY

According to embodiments of the present invention, a combined predictive analytics approach is presented, which utilizes unstructured data features and structural data features to generate predictions using multidimensional data. For a plurality of entities, a corpus of information is analyzed to extract unstructured information and chemical structural information to characterize the entity. For each entity of the plurality of entities, a semantic feature vector and a chemical structural feature vector are generated based on the extracted unstructured information and chemical structural information, wherein the semantic feature vector comprises the extracted unstructured information and the chemical structural feature vector comprises the extracted chemical structural information. An annotated entity feature vector is generated, for each entity, the annotated entity feature vector comprising the semantic feature vector and the chemical structural feature vector. A subset of entities from the plurality of entities is identified similar to an input entity feature vector based on a similarity score between the annotated entity feature vector and the input entity feature vector. The identified subset of entities is predicted to have a specified property or behavior in common based on the similarity score.

It is to be understood that the Summary is not intended to identify key or essential features of embodiments of the present disclosure, nor is it intended to be used to limit the scope of the present disclosure. Other features of the present disclosure will become easily comprehensible through the description below.

BRIEF DESCRIPTION OF THE DRAWINGS

Generally, like reference numerals in the various figures are utilized to designate like components. Through the more detailed description of some embodiments of the present disclosure in the accompanying drawings, the above and other features and advantages of the present disclosure will become more apparent.

DETAILED DESCRIPTION

Techniques are provided for combining chemical structure-based and unstructured text-based analytics for similarity-based comparison of entities for predictive analytics in a cognitive system. Feature vectors may be generated to represent the chemical structure-based information and the unstructured text-based information. Both types of information may be used (or in some cases, if an entity may be represented by one dimension of data, text or chemical structure, the entity may be analyzed in a multidimensional manner) for the comparison of entities and for predictive analytics applications.

Figure 1:
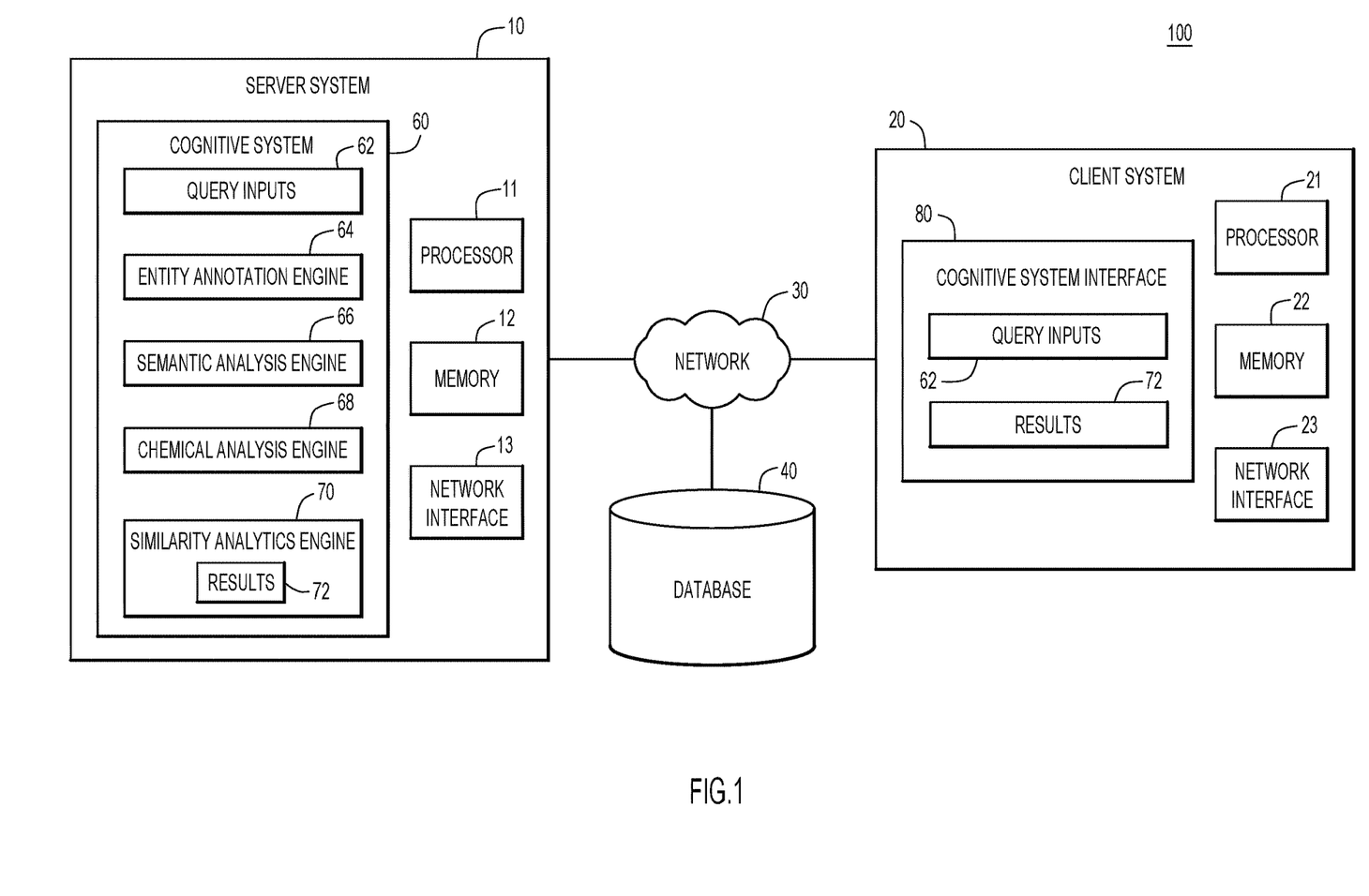
FIG. 1 is a block diagram of an example computing environment for predictive analytics in accordance with embodiments of the present disclosure.

An example environment for use with present invention embodiments is illustrated in FIG. 1. Specifically, the environment includes one or more server systems 10, and one or more client or end-user systems 20. Server systems 10 and client systems 20 may be remote from each other and may communicate over a network 30. The network may be implemented by any number of any suitable communications media (e.g., wide area network (WAN), local area network (LAN), Internet, Intranet, etc.). Alternatively, server systems 10 and client systems 20 may be local to each other, and may communicate via any appropriate local communication medium (e.g., local area network (LAN), hardwire, wireless link, Intranet, etc.).

Client systems 20 enable users to submit queries (e.g., queries for predictive analytics, etc.) to server systems 10 to generate predictions based upon an analysis of a large corpus of data (e.g., scientific data, scientific journals, publically and/or privately accessible chemical databases, databases of known pharmaceutical and/or biologic therapeutic compounds, databases/literature of known genes/DNA, databases/literature of expressed RNA, databases/literature covering proteomics, databases/literature covering metabolomics, etc.). In some aspects, users can input query terms, e.g., lung cancer genes, drugs to treat diseases, chemical compounds, proteins, biologics, etc.), and the system 100 will return a list of ranked entities, predicted to be related to the query based on a plurality of similarity metrics, e.g., encompassing structural data and unstructured data. In some aspects, entities determined to have the most similarity (e.g., as indicated by the similarity score) may be presented at the top of the list, with entities having less similarity may be presented at the end of the list. In other aspects, entities determined to have the most similarity (e.g., as indicated by the similarity score) may be presented at the bottom of the list, with entities having less similarity may be presented at the top of the list. Many different representations of ranked entities fall within the scope of the embodiments presented herein, and all are contemplated for use herein.

The server systems 10 include a cognitive system 60 to generate predictions based upon analysis of a large corpus of data. A database system 40 may store various types of information for the analysis (e.g., extracted structural features, extracted unstructured features, similarity scores, similarity matrices, etc.). For example, database 40 may store any data generated by server system 10, including unstructured feature vectors generated by the semantics analysis engine 66, structural feature vectors generated by the chemical analysis engine 68, similarity scores generated by the similarity analytics engine 70, and aspects of entity annotation generated by the entity annotation engine 64. The database system 40 may be implemented by any conventional or other database or storage unit, may be local to or remote from server systems 10 and client systems 20, and may communicate via any appropriate communication medium (e.g., local area network (LAN), wide area network (WAN), Internet, hardwire, wireless link, Intranet, etc.).

Server systems 10 and client systems 20 may be implemented by any conventional or other computer systems preferably equipped with a display or monitor, a base (e.g., including at least one hardware processor 11, 21 (e.g., microprocessor, controller, central processing unit (CPU), etc.), one or more memories 12, 22 and/or internal or external network interfaces or communications devices 13, 23, (e.g., modem, network cards, etc.) respectfully), along with optional input devices (e.g., a keyboard, mouse or other input device), and any commercially available and custom software (e.g., server/communications software, browser/interface software, etc.). Server system 10 comprises cognitive system 60, which includes query inputs 62, entity annotation engine 64, semantic analysis engine 66, chemical analysis engine 68, and similarity analytics engine 70 as described herein. In some embodiments, results 72 may comprise a ranked list of entities in response to a user query.

In other embodiments, a graphical representation of the results may be provided to the user. The client systems 20 may present a graphical user (e.g., GUI, etc.) or other cognitive system interface 80 (e.g., command line prompts, menu screens, etc.) to solicit information from users pertaining to the desired analysis, and may provide reports (e.g., lists, spreadsheets, graphical results, etc.) including analysis results 72 (e.g., predictive analytics including ranked entities corresponding to the query, individual similarity scores (e.g., chemical, text, etc.), structural features, unstructured features, visual representation of results, etc.).

Alternatively, one or more client systems 20 may analyze a corpus of documents to generate predictive analytics (e.g., a ranking of entities generated in response to a query, ranked based on features extracted from structural and unstructured data, etc.) when operating as a stand-alone unit. In a stand-alone mode of operation, the client system stores or has access to the data (e.g., data, including a natural language text corpus stored on database 40), and includes a cognitive system 60 to generate predictive analytics. The graphical user (e.g., GUI, etc.) or other interface 80 (e.g., command line prompts, menu screens, etc.) solicits information from a corresponding user pertaining to the desired documents and analysis for input into the cognitive system 60, and may provide reports and/or analysis results 72 to the user.

Cognitive system 60 may include one or more modules or units to perform the various functions of present invention embodiments described herein. The various modules (e.g., query inputs 62, entity annotation engine 64, semantic analysis engine 66, chemical analysis engine 68, and similarity analytics engine 70, etc.) may be implemented by any combination of any quantity of software and/or hardware modules or units, and may reside within memory 12 of the server for execution by processor 11.

In some aspects, query inputs 62 may include query terms provided by the user. In some cases, the query terms include one dimension of data (e.g., text-based data or structural data), while in other cases the query terms may include two or more dimensions of data (e.g., text-based data and structural data, etc.), Entity annotation engine 64 may utilize natural language processing to extract entities from a corpus of data. In some cases, the natural language processing component of the entity annotation engine may utilize machine learning to identify entities for extraction. In some cases, the entities may be annotated to be members of a class/type of entities, e.g., chemical compounds are annotated as being a type of particular chemical compound (e.g., an aminoketone, a benzodiazepine, etc.), gene names or protein names may be annotated as being implicated in a particular disease (e.g., BRCA1, BRCA2 are implicated in cancer, etc.) and so forth. In still other cases, types of diseases are extracted and annotated as diseases along with particular properties. In general, members of a class/type of entities will have a known relationship.

Annotation may occur in an automated or semi-automated manner. For instance, a machine learning system may be provided with a training data set, with which to learn and apply rules for classifying entities. A curator may review the annotations/classifications to verify that proper annotation/ classification has occurred, and additional training data may be provided in cases in which misclassifications are discovered.

It should be noted that the system and method presented herein may furthermore be extended to include types of entity-specific data representations other than the specific chemical structure-based data described herein, such as sequence data for proteins and other macromolecules, or may be extended to include entity-specific information for non-life sciences entities.

Semantic analysis engine 66 may generate semantic feature vectors describing the characteristics of the entities from analysis of the corpus of unstructured data, e.g., text based data. A feature vector for an entity may include information which links the entity to the development and progression of particular diseases, to the treatment of particular diseases, to text-based names of particular chemical structures, to other molecules or macromolecules that the entity binds to, or any other property that may be described in a text-based representation. For an entity (e.g., a chemical compound, a gene, a protein, a macromolecule, etc.) that is mentioned in a document, the context of the entity within the document can be semantically analyzed, e.g., decomposed (e.g., into nouns and verbs, etc.) into terms used in the local or global vicinity of the entity to establish the context of the entity. For example, NLP techniques include embedding words, aggregating terms locally, aggregating terms across the entire content of the document, determining the frequency of a term within a document, extraction of individual words or N-grams (phrases of length N), etc., which may be used to generate feature elements to include in the feature vector describing the entity For example, a feature value may be included to indicate how frequently a word occurs with a document or within the corpus of document, e.g., a feature element may be represented as <BRCA1, 23> to indicate that the term BRCA1 occurred twenty three times in a document. The feature element value may be normalized using a weighting scheme such as term frequency inverse document frequency (TFIDF) to ensure that frequently occurring words are not overly emphasized in the analysis.

Typically, stop words (words that commonly occur but are of little value in determining context such as "an", "of", "the", etc.) are filtered out, so that non-stop words are used to determine context.

In some aspects, feature vectors may be generated for individual documents. These feature vectors may be aggregated into a global feature vector that describes the context of the entity within a corpus of documents. Thus, the semantic analysis engine 66 captures the context of an entity in a document and/or across a corpus of documents, using NLP techniques including machine learning components, for any characteristic or feature that can be represented in a text format. Once semantic analysis engine 66 extracts and generates context-based feature vectors for an entity, the feature vectors may be stored in a repository, such as database 40.

In some embodiments, the semantic analysis engine 66 may comprise a machine learning component to identify and extract feature elements from annotated data generated by the entity annotation engine 64. In other approaches, statistical methods may be used to aggregate semantic data into feature elements from characteristics identified by NLP processing.

Chemical analysis engine 68 generates chemical structure feature vectors which capture aspects of the chemical structure of a molecule. The chemical feature vectors represents granular information of individual molecules.

Chemical structure-based feature vectors may include the use of chemical fingerprints, a common feature vector in the field of chemical informatics, which describes the presence, absence, or multiplicity of various atom and bond substructures within the chemical structure graph, for instance 'a nitrogen atom', 'a carbon atom double-bonded to an oxygen atom', or 'a carboxylic acid functional group,' and so on.

Chemical structure-based feature vectors may also include the use of any feature space defined by properties of the chemical structure or which may be derived from the chemical structure, for example molecular mass, counts of different atom types or functional groups, approximate calculated measures of molecular solubility, a list of the pairs of atoms that are bonded together in a chemical structure of the molecule, connectivity of atoms, distances between atoms, specific structural features that are common in molecules of a certain type, etc. Thus, chemical structure analysis engine 68 captures the structural aspects of a compound, and may be used to represent any characteristic or feature that can be represented or derived from the chemical structure.

Chemical analysis engine 68 may convert unstructured entities (e.g., a text name of a chemical compound entered by a user or a text name of a chemical compound discovered in the corpus of documents) into a computational format representing their corresponding chemical structure. Chemical structure feature vectors may be generated for each entity, and the chemical structure feature vectors may be stored in corresponding repositories, e.g., database 40, for extracted entities and user entered entities.

Chemical structures can be obtained in various ways, including but not limited to the propagation of chemical structure information for a given entity from the domain-relevant entity database (e.g., from a pre-existing database, or from expert-curated chemical structure information for an entity), as well as the algorithmic determination of chemical structure through cheminformatics software (e.g., dynamic generation of chemical structures of entities, which may not be known to environment 100 in advance, encountered during processing of the corpus of documents). For example, cheminformatics software can algorithmically generate a chemical structure from the name of a compound encountered in a text-based format during processing of the corpus of documents.

In other embodiments, physical features associated with the structure of an entity that can be computed (or simulated) and translated into a feature space can be included into a chemical structure feature vector, e.g., a 3D conformation, an energy of interaction, etc.

In some embodiments, the chemical analysis engine 68 may comprise a machine learning component to identify and extract feature elements from chemical structure data. In other approaches, statistical methods may be used to aggregate chemical structure data into feature elements from characteristics identified by chemical structural processing.

Predictive analytics methods may apply statistical or other predictive methods to the various chemical structure feature vectors (comprised of chemical structure feature elements) and semantic feature vectors (comprised of sematic feature elements) that describe an entity, to make predictions about the functionality or behavior of the entity. An entity may be represented by a plurality of feature elements from structural data and a plurality of feature elements from unstructured data. This information may be provided to similarity analytics engine 70 for analysis.

Similarity analytics engine 70 may generate a similarity matrix to compute similarity and other matrix statistics, e.g., a similarity score, etc. for two entities based on the semantic and chemical structure feature vectors. Feature elements may be weighted individually or as a group.

The similarity matrix can be used to create a network of connections between entities by connecting, for a first entity, a second entity determined to be the most similar (e.g., the N most similar) to the first entity. This type of connected network can be used, for example, to calculate a similarity score of a candidate entity to a given set of training entities, known to have a certain property. In this way, the similarity network can be used to infer new properties of an entity given a set of entities that are known to have a particular property. For example, in the context of drug repurposing, the system may use, as a training set, a group of drugs known to treat a specific disease. The system may predict that a particular drug may also be used to treat a disease, when the particular drug has a sufficient similarity, as determined by a similarity score, to a drug or a group of drugs known to treat the specific disease. In some aspects, the results are provided in a ranked listing, and/or in a visual form with nodes and connections, etc.

In some embodiments, a machine learning component may be integrated into the similarity analytics engine 70, to perform calculations on the matrix of similarities to generate comparisons or discover correlations absent in a non-learning type of approach.

In the multidimensional approaches provided herein, chemical and semantic feature vectors may be compared by the similarity analytics engine 70 (rather than using a single dimension of data) to provide a multidimensional measure of entity similarity. In some embodiments, the density of information may be vary among feature vectors. For example, the semantic feature vector may be sparse and may generate a relatively low score, e.g., in a range of 0.2 to 0.4, while in other embodiments, the chemical feature space may be dense, and may generate a relatively high score, e.g., in a range of 0.4 to 0.9. Thus, the semantic score may be combined with the chemical score to generate a score that reflects the combined similarity of entities across multiple dimensions when the respective feature vectors are of varying densities.

Figure 2:
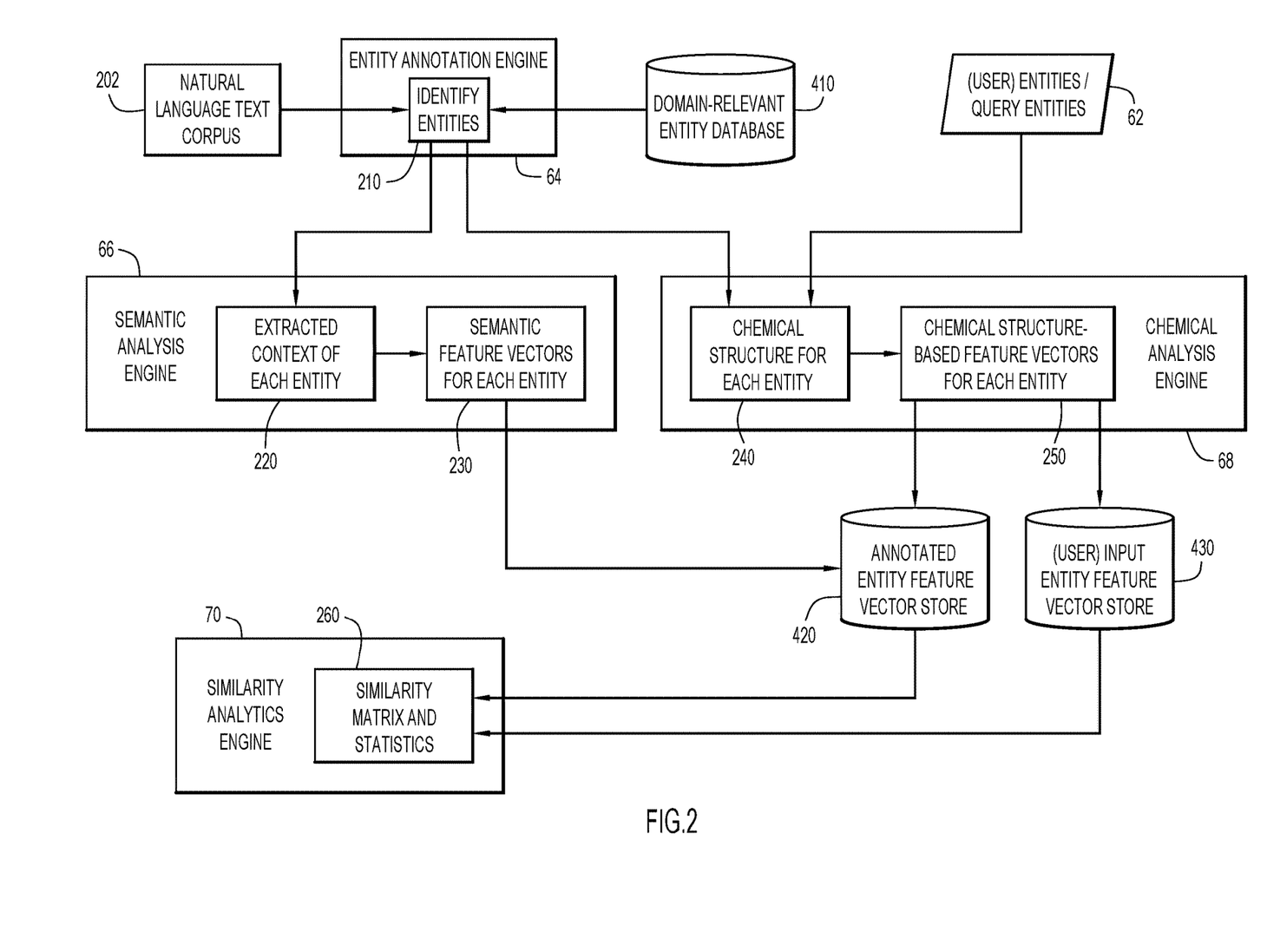
FIG. 2 is an illustration showing generation of structural and unstructured feature vectors along with generation of a similarity score, in accordance with embodiments of the present disclosure.

FIG. 2 shows an example illustration showing generation of structured and unstructured feature vectors along with generation of a similarity score, in accordance with embodiments of the present disclosure.

A natural language text corpus 202 may be processed by entity annotation engine 64 that identifies entities 210 from documents. In some aspects, the entity annotation engine 64 may store extracted information in database 40. In other aspects, entity annotation engine 64 may access domain relevant entities, e.g., an entity having a known relationship to another entity, stored in database 410 to use as inputs for analyzing the natural language text corpus. Entity annotation engine 64 may identify chemical structures obtained from databases comprising chemical structures or obtained from the corpus of information. For example, domain relevant entity database 410 may comprise the names of extracted entities (e.g., a gene name, a protein name, a chemical compound name, etc.) that may have been curated, and the entity annotation engine may use these domain relevant entities 210 as inputs to search for information pertaining to these specific entities within the corpus of documents. The extracted information (e.g., the entity, phrases surrounding the entity, entity in the context of the document, etc.) may be provided to semantic analysis engine 66 and chemical analysis engine 68 for creation of the respective feature vectors. In some embodiments, the entity annotation engine 64 may extract data from available databases and systems, may extract entities from documents provided by the user, or both. In some embodiments, the query may be performed against documents that have previously been processed by the entity annotation engine 64.

User input 62 may be inputs provided by a user, e.g., a disease name in combination with one or more chemical names, a disease name in combination with one or more chemical structures, etc. In some embodiments, users can specify a chemical component backbone, a portion of a chemical compound, or a functional group of a compound or of a macromolecule, an aspect of a chemical structure, rather than the entire molecule. In some embodiments, a portion of a chemical structure or macromolecular structure may be evaluated.

Present invention embodiments also provide for a user entering an experimental chemical structure, so that the system may be used for predictive analytics, e.g., determining which compound of a plurality of experimental compounds may be the most likely to have a therapeutic effect. A pharmaceutical company's experimental compound may have a structure known only to that company, which cannot be algorithmically determined, and therefore, needs to be provided by a user.

Accordingly, a user can input a novel entity not found in the NLP corpus (e.g., a novel chemical structure) and perform analytics upon it with respect to other entities, by expressing the entity as a chemical structure (e.g., either directly or by converting the entity to a chemical structure). Likewise, a user can input an entity that cannot be expressed as a chemical structure, and perform analytics on it, provided that the entity is present in the NLP corpus. The system may receive a user input, comprising structural and/or unstructured data, and may create an input entity feature vector comprising chemical structure-based features and/or semantic features. Chemical structure-based features may be generated by chemical analysis engine 68, while semantic features may be obtained from semantic features vectors generated by semantic analysis engine 66. For example, if a user entered "Parkinson's Disease" as part of a query, then the system would search for a semantic feature vector corresponding to Parkinson's Disease.

In some aspects, the system may indicate which compounds are candidates for experimental testing, and which have already been experimentally verified.

Semantic analysis engine 66 may be used to generate semantic feature vectors 230 based on the extracted context of an entity 220. For example, a context can be determined locally (by extracting words local to entities) or globally (evaluating the context of an entity globally within a document) or by user specified metrics, as provided herein. These characteristics may be stored as feature elements within a semantic feature vector corresponding to the entity.

Chemical analysis engine 68 may be used to generate chemical structure feature vectors 250 based on characteristic of chemical structures. Chemical structures may be generated dynamically, by identifying entities (e.g., chemical names) within the corpus of documents 202, and utilizing chemical informatics software to generate chemical structures from a text-based chemical name. The computer generated chemical structure may be used to generate chemical feature elements within a chemical feature vector for an entity. In some cases, chemical structures may be present in the corpus of documents and machine learning techniques involving image recognition may be used to identify and/or extract the chemical structures from the document.

The semantic feature vector 230 and the chemical structure feature vector 250 may be stored in the annotated entity feature vector store 420. In some embodiments, the semantic feature vector and the chemical structure feature vector are stored as separate vectors, while in other embodiments, the semantic feature vector and the chemical structure feature vector are combined into a single vector per entity. User input entity vectors, generated from user input 62, may be stored in user input entity feature vectors 430.

To generate a prediction regarding how similar two entities are, the semantic feature vector 230 and the chemical structure feature vector 250 are provided to the similarity analytics engine 70 along with the user input 430, which serves as the query. The similarity analytics engine 70 generates a similarity matrix and computes corresponding statistics to identify responses to user queries, e.g., chemical compound predicted to treat a disease or disorder. The results can be visualized through the cognitive system interface 80.

Thus, in summary and as shown in FIG. 2, a natural language corpus 202, comprising free text can be analyzed with NLP processing. Entities can be extracted, annotated, and stored as domain relevant concepts (e.g., groups of chemical compounds, genes, diseases, etc. stored in groups with particular relationships). The output of the entity annotation engine 64 may flow down two separate paths, into the semantic analysis engine 66 to understand local/global context of an entity in a document or corpus of documents, represented as an unstructured feature vector, or into a chemical analysis engine 68 after being converted into a chemical structure, represented as a chemical structure feature vector. Present embodiments allow for compound names (e.g., as user input or in an unstructured document) to be automatically converted by system 100 into a chemical structure representation, and from that representation, a chemical structure feature vector can be generated.

The generated feature vectors may be stored, and provided to similarity analytics engine 70 for analysis, which computes a similarity score based upon the combination of the unstructured and structural feature vectors. Similarity analytics engine 70 may compare entities using a similarity matrix (e.g., a pairwise matrix) to compute a similarity score based on the combined semantic and chemical structure feature spaces.

Figure 3:
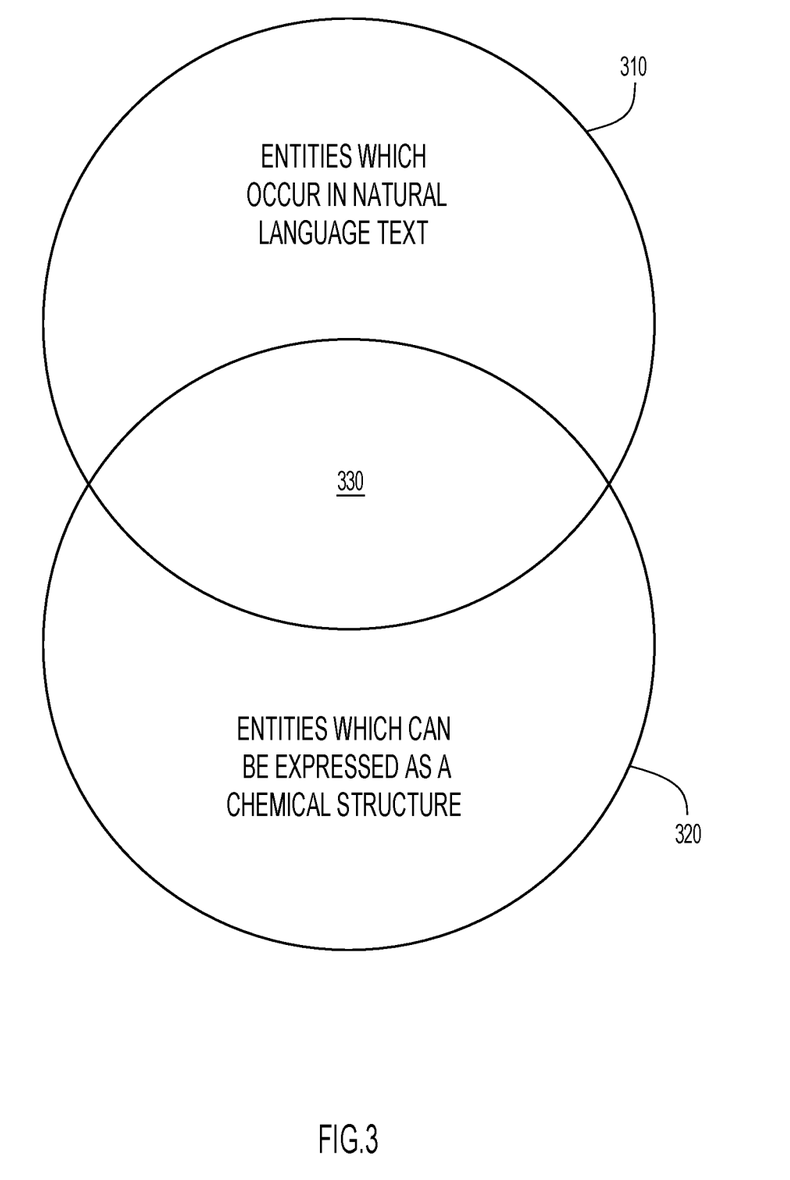
FIG. 3 is a Venn diagram showing overlapping and non-overlapping data features represented by structural and unstructured data, according to embodiments of the present disclosure.

FIG. 3 is a Venn diagram showing overlapping and non-overlapping entity descriptions, represented by structural data and unstructured data, according to embodiments of the present disclosure. Region 310 shows entities which may be described as unstructured data, e.g., occurring in natural language text. Region 320 shows entities which may be described as chemical structural data.

Some entities may be described in either format, as shown by the region of overlap 330, which represents entities that can equivalently be expressed as text or a chemical structure.

Present invention embodiments allow predictive analytics to be performed on entities that are queried in different feature spaces. By converting an entity from one dimension into another dimension, e.g., chemical structure to text name or from text name to chemical structure, the two feature spaces can be combined, allowing insights to be derived from a combined feature space, that are not derivable from a single feature space. For example, two compounds that are similar in their chemical structure, e.g., in the same class of molecules, may be discussed in widely different contexts within the literature. This may lead to insights, e.g., identifying features present within the first compound that are not present in the second compound that may lead to the prediction of novel types of compounds useful for treating a disease. As another example, two compounds may be discovered within the same context (e.g., treating the same disease) that have different chemical structures, which may lead to predictions regarding a fundamental behavior that transcends predictions based solely on chemical structural similarity.

In some aspects, to allow correlation between a chemical structure feature vector and a semantic feature vector that both correspond to the same entity, the chemical structure feature vector may contain an identifier (e.g., an index, a pointer, or other reference) that indicates to environment 100 that the chemical structure feature vector and the semantic feature vector represent the same entity. In other aspects, to allow correlation between a chemical structure feature vector and a semantic feature vector that both correspond to the same entity, the semantic feature vector may contain an identifier (e.g., an index, a pointer, or other reference) that indicates to environment 100 that the chemical structure feature vector and the semantic feature vector represent the same entity. This approach or any suitable equivalent thereof may ensure that the similarity analytics engine combines the semantic and chemical structure feature vectors for a given entity, to perform a multi-dimensional computation.

In some embodiments, an entity (as extracted by the entity annotation engine) may be represented as a text-based structure. In some embodiments, an entity (as extracted by the entity annotation engine) may be represented as a chemical structure. According to the embodiments presented herein, the system can convert an entity represented by one of these types of data representations into the other type (if such a representation exists) to perform complex analytics processing utilizing the techniques provided herein.

Figure 4:
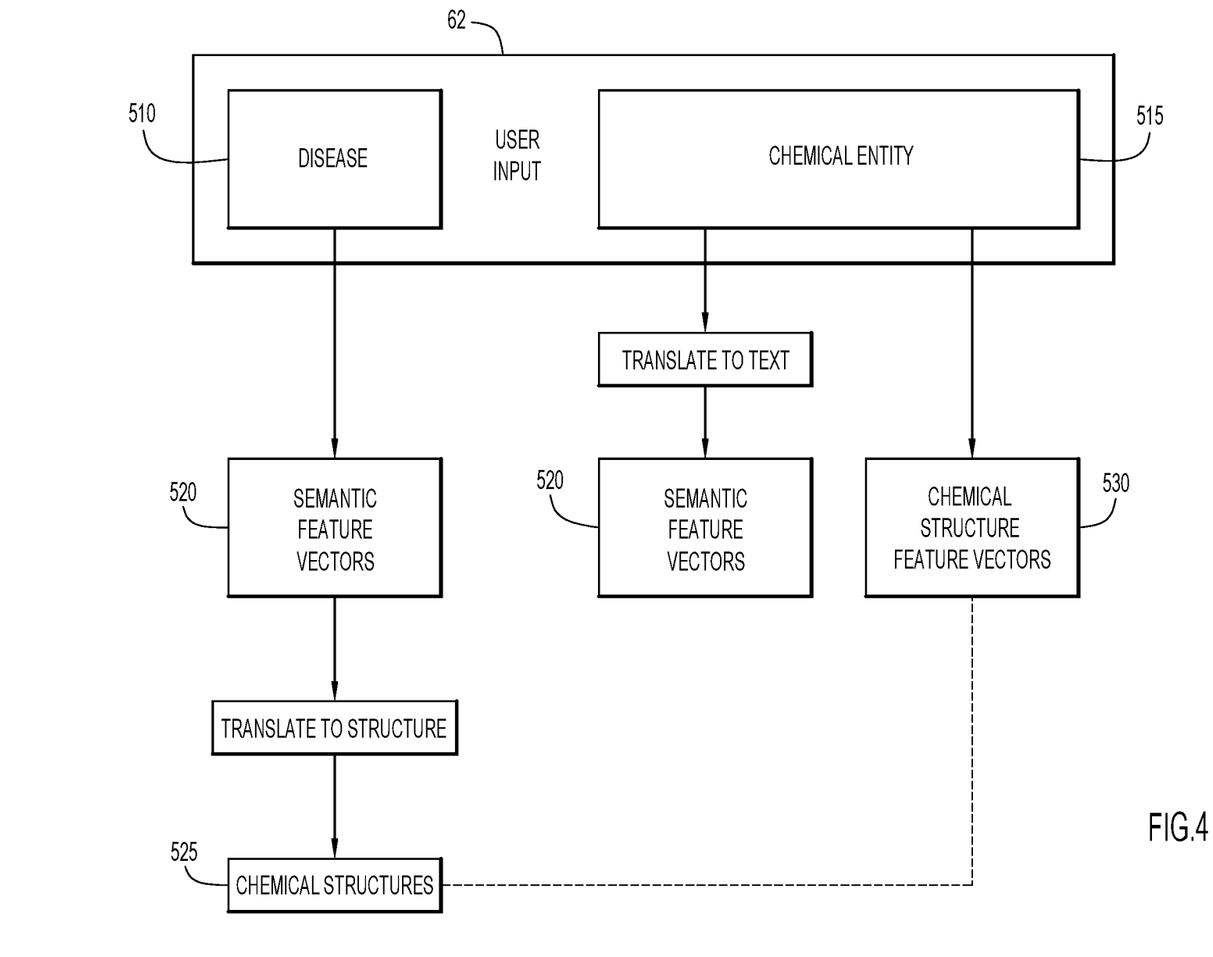
FIG. 4 is an example of transforming data to generate complex predictive analytics, according to embodiments of the present disclosure.

FIG. 4 is an example of performing complex predictive analytics in a multidimensional manner on an entity limited to one dimension of data, according to embodiments of the present disclosure. In this example, a user may generate a query, user input 62, corresponding to a particular disease 510 and a particular chemical compound 515 in order to generate predictions as to whether a chemical compound may be useful for treating a particular disease.

For example, five different compounds (chemical 515) and three different diseases (disease 510) may be entered as user input 62. In some embodiments, diseases are not translated into a chemical structure (as such representations do not generally exist). Therefore, the disease may be searched against semantic feature vectors 520, to determine whether the semantic feature vectors reference the disease, based on analysis of a corpus of documents. If a match is found, and the semantic feature vector references the disease, then the semantic feature vector may be further evaluated to determine whether the disease is associated with names of chemical structures known to treat the disease. If present, in some embodiments, the chemical names may be translated into chemical structures 525 for comparison to chemical structure feature vectors 530. Thus, in this example, a one dimensional entity, e.g., a disease, may be analyzed in a multidimensional capacity, provided that the corpus of documents provide a way to link chemical structures to the disease.

Chemical compounds 515 may be searched against the chemical structure feature vectors 530 to determine if a match for the chemical structure is present. Chemical compounds 515 may also undergo translation to text, e.g., to represent a chemical compound as an equivalent chemical text-based name, and may be searched against semantic feature vectors 520 to determine if a match for the chemical name is present. In this example, translations from a chemical structure to an equivalent semantic text-based representation, allows for analysis to be performed on documents which may represent a chemical structure only as a chemical name.

In some aspects, a compound name or a disease may be generalized if particular matches are not found (e.g., if a search for ALS does not return suitable results, then the term could be broadened to sclerosis, or if a search for a specific chemical name does not return suitable results, then the name could be broadened to the chemical backbone or functional portion of the molecule).

Including semantic feature vectors provide a mechanism to relate diseases (unstructured data) to candidate chemical structures that may be useful for treatment.

Figure 5:
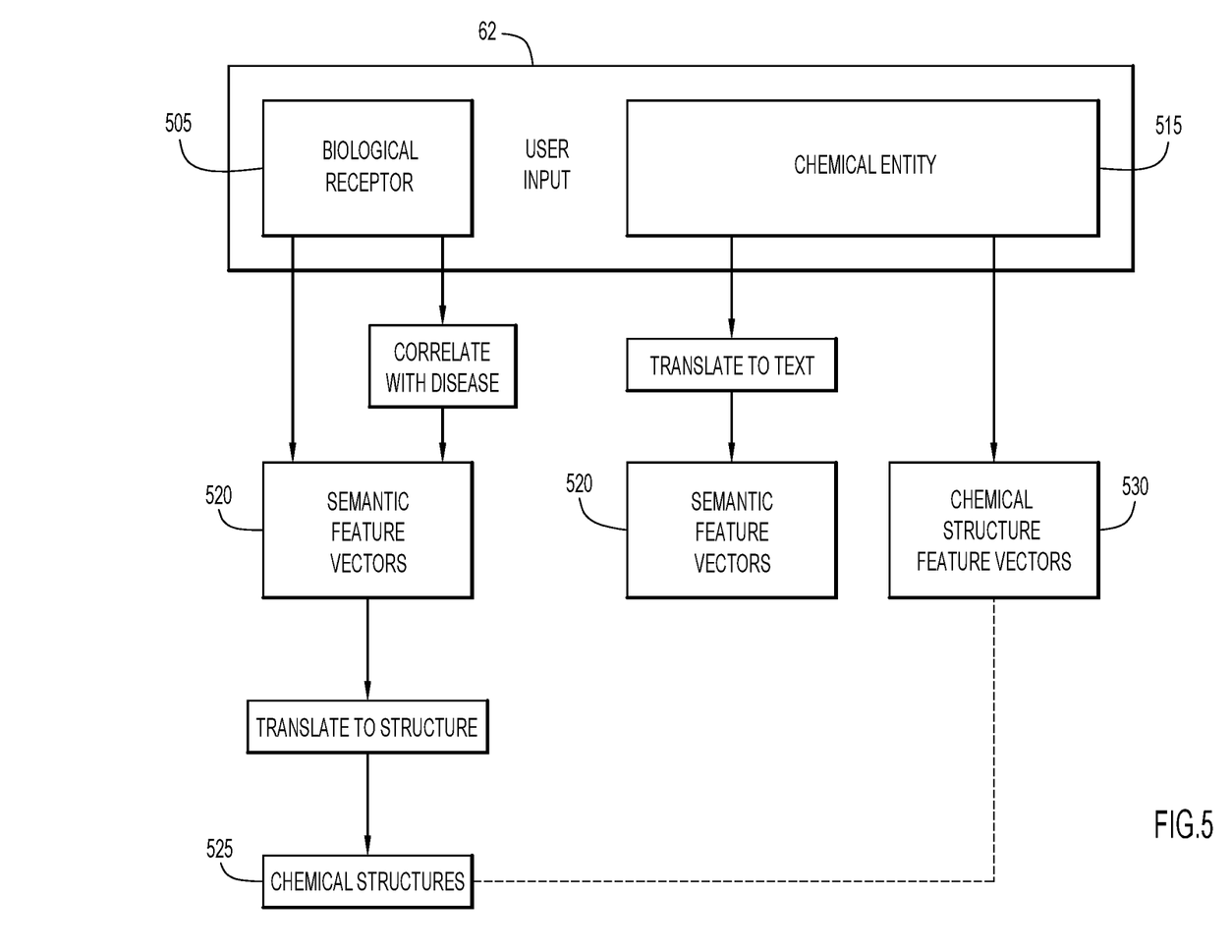
FIG. 5 is another example of transforming data to generate complex predictive analytics, according to embodiments of the present disclosure.

FIG. 5 is another example of transforming data to generate complex predictive analytics, according to embodiments of the present disclosure. In this example, a chemical entity 515 and a name of a biological receptor 505 implicated in a disease, may be entered as user input 62.

Similar to FIG. 4, chemical entity 515 may undergo translation to text, e.g., to represent a chemical compound as an equivalent chemical name, and may be searched against the semantic feature vectors 520 to determine if a match for the chemical name is present. Chemical entity 515 may additionally be searched against the chemical structure feature vectors 530 to determine if a match for the chemical structure is present.

Biological receptor 505 may be searched against semantic feature vectors 520, to determine whether any semantic feature vectors reference the biological receptor, based on analysis of a corpus of documents. If a match is found, the semantic feature vector may be further evaluated to determine whether the receptor is associated with names of chemical compounds that bind to the receptor. If present, in some embodiments, the chemical names may be translated into chemical structures 525 for comparison to chemical structure feature vectors 530.

If the target biological receptor is associated with a disease, the semantic feature vectors may be searched for additional names of chemical entities useful in treating the disease. If a match is found, the names of the chemical entity may be translated into chemical structures 525 for comparison to chemical structure feature vectors 530.

Thus, according to present invention embodiments, the chemical entities may be transformed from a chemical name to a chemical structure and vice versa to consider a broader volume of data in a similarity analysis. Additionally, features in the sematic feature space may be correlated, e.g., linking a disease to a name of biological receptor and vice versa, to broaden the types of chemical entities that may be considered in predicting new compounds which may be useful in the treatment of a disease.

Figure 6:
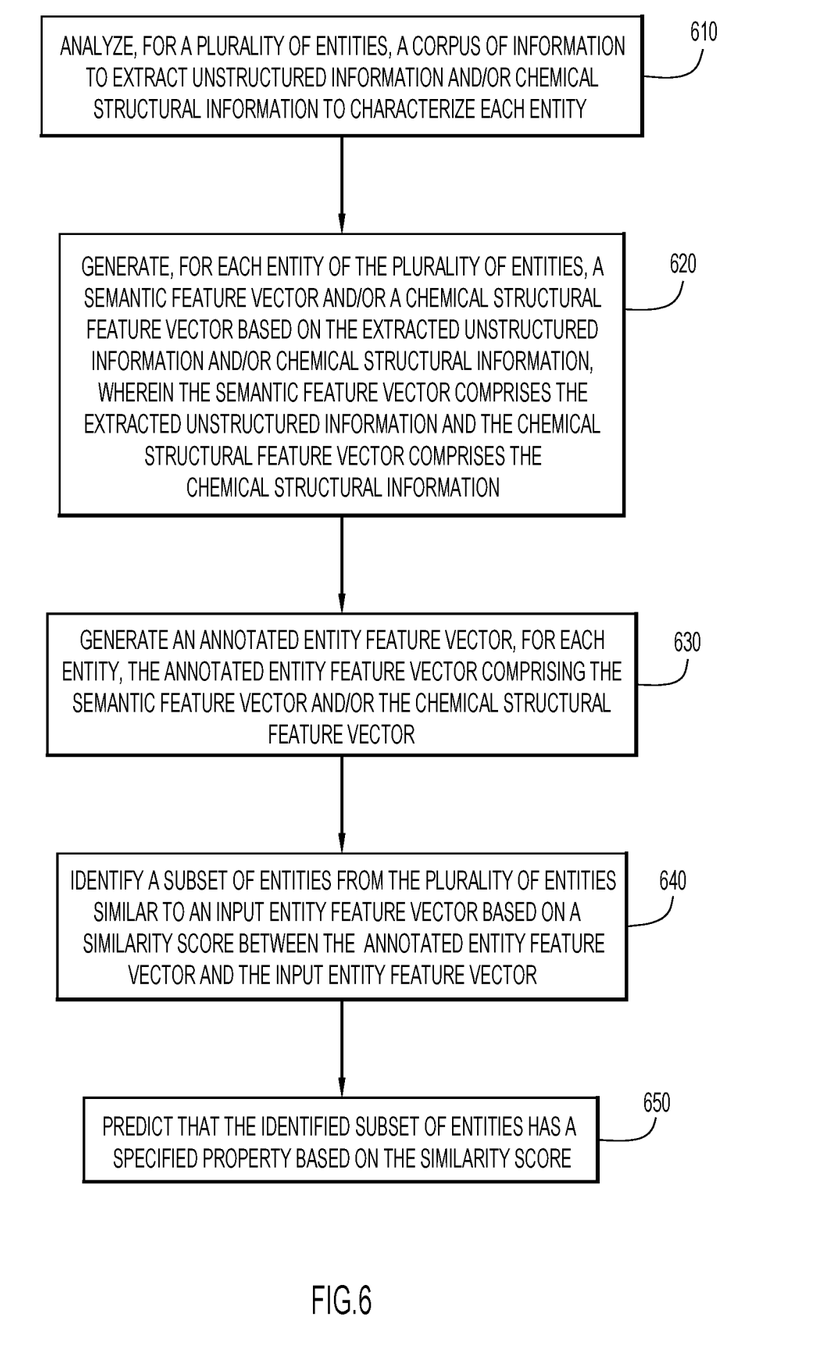
FIG. 6 is a flowchart of operations for making predictions using a combination of structured and unstructured data, according to embodiments of the present disclosure.

FIG. 6 shows a flowchart of operations for making predictions using a combination of structural and unstructured data, according to embodiments of the present disclosure. At operation 610, for a plurality of entities, a corpus of information is analyzed to extract unstructured information and/or chemical structural information to characterize the entity. At operation 620, for each entity of the plurality of entities, a semantic feature vector and/or a chemical structural feature vector is generated based on the extracted unstructured information and/or chemical structural information, wherein the semantic feature vector comprises the extracted unstructured information and the chemical structural feature vector comprises the extracted chemical structural information. At operation 630, for each entity, an annotated entity feature vector is generated, wherein the annotated entity feature vector comprises the semantic feature vector and/or the chemical structural feature vector. At operation 640, a subset of entities is identified from the plurality of entities similar to a user input entity feature vector based on a similarity score between the annotated entity feature vector and the user input entity feature vector. At operation 650, the identified subset of entities are predicted to have a specified property, e.g., useful for the treatment of a particular disease or disorder, based on the similarity score.

Accordingly, present invention embodiments may be used as part of a predictive analytics system and/or methodology to generate predictions based upon the analysis of a corpus of information.

Present invention embodiments allow for both unstructured data and structured data corresponding to an entity to be searched across a corpus of data. Additionally, chemical structures may be translated into a format compatible with searching a semantic feature space, and semantic inputs may be translated into a chemical structural feature space. Accordingly, unstructured data to unstructured data, structural data to structural data, unstructured data to structural data, and structural data to unstructured data searches may each be performed to make inferences and predictions on information from processing millions or tens of millions of documents. These techniques allow novel relationships to be discovered from searching complex feature spaces that are not otherwise evident. Additionally, such novel relationships may be discovered, in real time or near real time, as inputs may be changed and corresponding weights of inputs may be adjusted in real time to tailor search results to particular queries.

The embodiments provided herein allow for complex predictions to be generated by utilizing multi-dimensional data. These techniques may be utilized to provide a more complete and robust predictive analytics capability using both chemical and semantic feature vectors. Predictions may be tested experimentally, and the results of the predictions provided to the cognitive system 60, in order to continually improve and refine predictive abilities.

The embodiments provided herein may be applied to the field of chemical informatics, wherein the entities may be small molecules, as well as the field of biologics, wherein the entities may be genes, proteins, antibodies, peptides, or any other biologic macromolecule for which structural information or semantic information may be available. Predictive analytics may be used to identify molecules involved in the formation and/or progression of a disease or disorder as well as entities that may be useful in treating said diseases or disorders.

It should be noted that the system and method presented herein can furthermore be extended to include types of entity-specific data representation other than the specific chemical structure-based data described herein, such as sequence data for biological macromolecules including nucleotides, proteins, biologic therapeutics, etc., or equivalent entity-specific information for non-life sciences domain adaptation as necessary. Furthermore the architecture of predictive analytics described herein, enabling the use of two distinct types of data in the analytics methodology, can be extended to allow for three or more types of data, within the same approach described herein.

For biological macromolecules, semantic and/or chemical structural feature vectors may be constructed to capture characteristics of the biological macromolecule. In some cases, it may be more convenient to represent the biological entity with a semantic feature vector, e.g., for large molecules. For example, complex macromolecules that are difficult to represent in an atomistic structural format may be represented in a text-based manner, e.g., as a sequence listing, or a gene or protein name. In other embodiments, it may be more convenient to represent the biological macromolecule with a chemical structural feature vector (e.g., for smaller molecules or portions of molecules). Types of semantic features that may be useful to include about biological macromolecules may include small molecules that bind to the macromolecule, amino acid residues and positions that are involved in binding, etc. Types of chemical structural features that may be useful to include about biological macromolecules may include distances between atomics, positions of atoms, data obtained from crystallographic studies, etc.

Thus, a user may compare chemicals with diseases (using NLP semantics), and may compare chemicals to each other (using NLP semantics and/or structures) where one chemical compound is presented as a structure and the other chemical compound is presented as a text name. Moreover, compounds may be predicted to treat a particular disease. For example, a compound similar to another compound, not discussed in context of Parkinson's disease, could be predicted to treat a disease such as Parkinson's disease.

It will be appreciated that the embodiments described above and illustrated in the drawings represent only a few of the many ways of implementing embodiments for combining unstructured with structural data for improved predictive analytics.

It will also be appreciated that the methods provided herein are implemented by a computer as part of a cognitive system.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, cognitive system 60, cognitive system interface 80, etc.). These systems may include any types of monitors and input devices (e.g., keyboard, mouse, voice recognition, etc.) to enter and/or view information.

It is to be understood that the software (e.g., cognitive system 60, cognitive system interface 80, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., cognitive system 60, cognitive system interface 80, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., identified entities, annotated entities, chemical structures, query inputs, semantic feature vectors, chemical feature vectors, similarity scores, similarity matrix and statistics, results of predictive analytics, ranking of similar entities, etc.). The database system may be implemented by any number of any conventional or other databases, data stores or storage structures (e.g., files, databases, data structures, data or other repositories, etc.) to store information (e.g., identified entities, annotated entities, chemical structures, query inputs, semantic feature vectors, chemical feature vectors, similarity scores, similarity matrix and statistics, results of predictive analytics, ranking of similar entities, etc.). The database system may be included within or coupled to the server and/or client systems. The database systems and/or storage structures may be remote from or local to the computer or other processing systems, and may store any desired data (e.g., identified entities, annotated entities, chemical structures, query inputs, semantic feature vectors, chemical feature vectors, similarity scores, similarity matrix and statistics, results of predictive analytics, ranking of similar entities, etc.).

The present invention embodiments may employ any number of any type of user interface (e.g., Graphical User Interface (GUI), command-line, prompt, etc.) for obtaining or providing information (e.g., identified entities, annotated entities, chemical structures, query inputs, semantic feature vectors, chemical feature vectors, similarity scores, similarity matrix and statistics, results of predictive analytics, ranking of similar entities, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The report may include any information arranged in any fashion, and may be configurable based on rules or other criteria to provide desired information to a user (e.g., identified entities, annotated entities, chemical structures, query inputs, semantic feature vectors, chemical feature vectors, similarity scores, similarity matrix and statistics, results of predictive analytics, ranking of similar entities, etc.).

The present invention embodiments are not limited to the specific tasks or algorithms described above, but may be utilized for any system in which multidimensional analysis is desired, e.g., for entities that have a chemical and a semantic component, or for entities in which there is a need to relate a chemical and a semantic component.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method, in a cognitive data processing system comprising at least one processor and at least one memory, the at least one memory comprising instructions executed by the at least one processor to cause the at least one processor to implement a predictive analytics system that combines structural features and unstructured features, the method comprising:
analyzing, for a plurality of entities, a corpus of information to extract unstructured information and chemical structural information to characterize each entity;
generating, for each entity of the plurality of entities, a semantic feature vector and a chemical structural feature vector based on the extracted unstructured information and chemical structural information, wherein the semantic feature vector comprises the extracted unstructured information and the chemical structural feature vector comprises the chemical structural information indicating atom and bond substructures within a chemical structure graph for the entity;
generating an annotated entity feature vector, for each entity, the annotated entity feature vector comprising the semantic feature vector and the chemical structural feature vector;
identifying a subset of entities from the plurality of entities similar to an input entity feature vector based on a similarity score between the annotated entity feature vector and the input entity feature vector, wherein the input entity feature vector includes semantic features and chemical structure-based features of an input entity; and
predicting that the identified subset of entities has a specified property based on the similarity score.

2. The method of claim 1, wherein determining a similarity score further comprises:
constructing, using a similarity analytics engine, a similarity matrix based on features of the annotated entity feature vector and features of the input entity feature vector; and
computing the similarity score, wherein the similarity score reflects a similarity of feature elements between the annotated entity feature vector and the input entity feature vector.

3. The method of claim 1, further comprising:
receiving a query comprising a query entity without a chemical structural representation;
searching semantic feature vectors of the plurality of entities for a match to the query entity;
when a match is identified, searching the matching semantic feature vector for a name of an associated chemical compound;
converting automatically the name of the chemical compound to an equivalent chemical structure; and
computing the similarity score, wherein the similarity score includes a chemical structural feature vector identified based on the equivalent chemical structure.

4. The method of claim 1, further comprising:
receiving a query comprising a name of a chemical compound;
converting automatically the name of the chemical compound to an equivalent chemical structure;
computing the similarity score, wherein the similarity score includes a chemical structural feature vector identified based on the equivalent chemical structure.

5. The method of claim 1, further comprising:
providing a ranked listing of the subset of entities highest in similarity to the input entity feature vector.

6. The method of claim 1, wherein the plurality of entities includes one or more from a group of a chemical compound, a gene, a disease, a drug, and a biologic compound.

7. The method of claim 1, wherein the semantic feature vector comprises strings of text characterizing a context of the entity globally or locally within a document.

\* \* \* \* \*